United States Patent [19]

Standke et al.

[11] Patent Number: 5,932,757
[45] Date of Patent: Aug. 3, 1999

[54] MIXTURE OF OLIGOMERS OF CONDENSED ALKYLALKOXYSILANES

[75] Inventors: Burkhard Standke, Loerrach; Roland Edelmann, Wehr; Albert Frings, Rheinfelden; Michael Horn, Rheinfelden; Peter Jenkner, Rheinfelden; Ralf Laven, Niederdossenbach; Jaroslaw Monkiewicz, Rheinfelden; Lothar Elfenthal, Langenfeld; Hans-Hermann Luginsland, Leverkusen, all of Germany

[73] Assignee: Huls Aktiengesellschaft, Marl, United Kingdom

[21] Appl. No.: 08/877,556

[22] Filed: Jun. 17, 1997

[30] Foreign Application Priority Data

Jun. 17, 1996 [DE] Germany ............... 196 24 032

[51] Int. Cl.$^6$ ................ C07F 7/08; C07F 7/18
[52] U.S. Cl. ............ 556/457; 556/458; 427/387
[58] Field of Search ............... 556/457, 458; 427/387

[56] References Cited

U.S. PATENT DOCUMENTS

| | | | |
|---|---|---|---|
| 4,950,779 | 8/1990 | Wengrovius et al. | 556/457 |
| 5,346,968 | 9/1994 | Haas | 556/457 X |
| 5,348,760 | 9/1994 | Parker et al. | |
| 5,543,173 | 8/1996 | Horn, Jr. et al. | |
| 5,563,231 | 10/1996 | Barringer et al. | 556/457 X |

FOREIGN PATENT DOCUMENTS

| | | |
|---|---|---|
| 0 049 365 | 4/1982 | European Pat. Off. |
| 0 518 057 | 12/1992 | European Pat. Off. |
| 0 579 453 | 1/1994 | European Pat. Off. |
| 0 675 128 | 10/1995 | European Pat. Off. |
| 0 716 127 | 6/1996 | European Pat. Off. |
| WO 92/06101 | 4/1992 | WIPO. |

OTHER PUBLICATIONS

Jack K. Crandall et al, "Siloxanes from the hydrolysis of isopropyltrimethoxysilane" *Journal of Organometallic Chemistry*, 489 (1995) 5–13.

*Primary Examiner*—Paul F. Shaver
*Attorney, Agent, or Firm*—Oblon, Spivak, McClelland, Maier & Neustadt, P.C.

[57] ABSTRACT

A mixture of oligomers of alkylalkoxysilanes condensed in the chain and/or cyclic form, said mixture of oligomers containing less than 2% by weight of free alcohols and the condensed alkoxysilanes satisfying formula I:

$$R'O+\left[\underset{\underset{OR'}{|}}{\overset{\overset{R}{|}}{Si}}-O\right]_x R', \quad (I)$$

wherein R is an alkyl group having 3 to 18 carbon atoms, and each R' is a member (i) selected from the group consisting of methyl, ethyl or hydrogen, or is (ii) methyl or hydrogen, or is (iii) ethyl or hydrogen, the degree of oligomerization being in the range $2 \leq x \leq 20$ and the quotient of the molar ratio [Si/alkoxy group]$\geq 1$; and/or satisfying formula II:

$$\left[\underset{\underset{OR'}{|}}{\overset{\overset{R}{|}}{Si}}-O\right]_x, \quad (II)$$

in which R is an alkyl group having 3 to 18 carbon atoms, and each R' is a member (i) selected from the group consisting of methyl, ethyl or hydrogen, or is (ii) methyl or hydrogen or is (iii) ethyl or hydrogen, the degree of oligomerization being $x \geq 3$ and the quotient of the molar ratio [Si/alkoxy group]$\geq 1$.

13 Claims, No Drawings

MIXTURE OF OLIGOMERS OF CONDENSED ALKYLALKOXYSILANES

BACKGROUND OF THE INVENTION

1. Field of the Invention

The present invention relates to mixtures of oligomers of alkylalkoxysilanes condensed in the chain and/or cyclic form, to a process for their preparation and their use.

2. Description of the Background

Alkyltrialkoxysilanes release alcohol on hydrolysis. Quantitatively, the alcohol, which is formed as a product of hydrolysis is, for example, in the case of octyltriethoxysilane, around 50% by weight of the trialkoxysilane used. Because of this fact, many potential applications for the alkyltrialkoxysilanes remain closed or are adversely affected, e.g. because of the explosion-proofing precautions required or for ecological reasons, with the keyword. The keyword here then is VOC=volatile organic compounds. However, from the applications viewpoint, in many cases it would be desirable to have substances available which have properties similar to those of the pure alkyltrialkoxysilanes, without having to accept the above disadvantages. Substances of this type could be used, in particular, in rendering mineral surfaces hydrophobic.

European Patent Application No. 0 518 057 discloses mixtures of siloxane oligomers having a degree of oligomerization of 0 to 8, with the siloxanes containing per Si atom at most one vinyl group and methoxy or ethoxy groups, with or without alkyl groups having 1 to 18 carbon atoms. In addition, 0 518 057 Al discloses a process for preparing these siloxane mixtures. The siloxane mixtures, which are distinguished because they have vinyl functional groups, are suitable, in particular, as crosslinking agents in the preparation of cable covering compounds based on thermoplastic polyolefins and for similar applications in association with crosslinkable organic substances.

SUMMARY OF THE INVENTION

Accordingly, one object of the present invention is to provide a liquid which is suitable for application in particular, to mineral surfaces and which substantially prevents wetting of the mineral surfaces by a hydrophilic liquid, for example, water. That is, the applied liquid renders the mineral surfaces hydrophobic. Upon application of the liquid to mineral surfaces and the addition of water, a markedly lesser quantity of alcohol is released than when alkyltrialkoxysilanes in concentrated form are used under corresponding conditions.

Briefly, this object and other objects of the present invention as hereinafter will become more readily apparent can be attained by a mixture of oligomers of alkylalkoxysilanes condensed in the chain and/or cyclic form, in which the mixture of oligomers contains less than 2% by weight of free alcohol and the condensed alkoxysilane satisfies formula I:

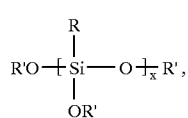

wherein R is an alkyl group having 3 to 18 carbon atoms, preferably 4 to 16 carbon atoms, very particularly preferably 6 to 10 carbon atoms, and all R' groups are (i) members selected from the group consisting of methyl, ethyl or hydrogen, or are (ii) methyl or hydrogen, or (iii) are ethyl or hydrogen, the degree of oligomerization being in the range $2 \leq x \leq 20$ and the quotient of the molar ratio [Si/alkoxy group]$\geq 1$;

and/or satisfies formula II:

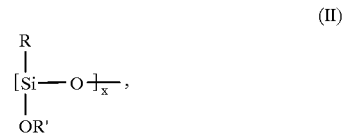

wherein R is an alkyl group having 3 to 18 carbon atoms. preferably 4 to 16 carbon atoms, very particularly preferably 6 to 10 carbon atoms, and all R' groups are (i) members selected from the group consisting of methyl, ethyl or hydrogen, or are (ii) methyl or hydrogen, or are (iii) ethyl or hydrogen, the degree of oligomerization being $x \geq 3$ and the quotient of the molar ratio [Si/alkoxy group]$\geq 1$.

DETAILED DESCRIPTION OF THE PREFERRED EMBODIMENTS

It has now been found that, for example, by the controlled hydrolysis and condensation of octyltriethoxysilane in the presence of an acid catalyst and subsequent removal by distillation of the alcohol produced by hydrolysis under reduced pressure, the work-up by distillation of the reaction mixture proceeding under substantially mild conditions, a low-viscosity mixture of octylethoxysiloxanes having a flashpoint of 125° C. is obtained in which the content of ethoxy groups is less than 20% by weight and the content of free ethanol is less than 1.5% by weight in comparison to pure octyltriethoxysilane which has a flashpoint of 109° C. The mixtures of oligomers of the invention are outstandingly suitable for rendering mineral surfaces hydrophobic without substantial amounts of alcohol being released by hydrolysis, in contrast to the use of alkyltrialkoxysilanes in concentrated form.

The mixtures of oligomers of the present invention preferably have a content of alkoxy groups of greater than 0.01% by weight and less than 20% by weight, each of the values being based on the weight of the mixture of oligomers present.

In addition, the mixtures of oligomers of the present invention preferably contain alkyl groups, denoted by R, each having the same chain length. In particular, R is an octyl group.

Preferably, the mixtures of oligomers of the present invention have a viscosity of less than 100 mPa·s.

The present invention also relates to the process for preparing a mixture of oligomers by hydrolysis and condensation of alkyltrialkoxysilanes, where the silanes used bear alkyl groups having 3 to 18 carbon atoms and methoxy and/or ethoxy groups as alkoxy groups, by reaction with more than 1 mol of water per 1 mol of Si and using HCl as catalyst, and with work-up by distillation of the resulting reaction mixture under reduced pressure at a bottom temperature of less than 95° C.

In the process according to the invention, the hydrolysis and condensation of the alkyltrialkoxysilanes are suitably carried out with the use of methanol and/or ethanol as diluent as well as solvent. The amount of solvent is generally chosen so that a single-phase mixture is formed.

For the hydrolysis of octyltriethoxysilane by the present process, for example, 1.2 mol of water per 1 mol of silane can be used.

The hydrolysis catalyst in the reaction medium can generally be removed again virtually quantitatively in the present process during the later workup by distillation of the reaction mixture. The catalyst is preferably HCl. However, other acids can also be used as catalyst.

The hydrolysis and condensation reaction is generally conducted in the present process under mild conditions, preferably at a temperature in the range 10 to 80° C., particularly preferably 30 to 78° C. The reaction can also be carried out under a protective gas, and normally under atmospheric pressure.

The hydrolysis and condensation reaction is preferably conducted with stirring over a period of 1 to 2 hours.

The reaction mixture thus obtained is worked-up by distillation under reduced pressure. During work-up, likewise under substantially mild conditions, the majority of the amount of free alcohol is removed by any convenient manner. At the same time, the catalyst component is discharged conjointly. In the work-up by distillation, the bottom temperature should, in particular, not be above 90° C. Preferably, the reaction mixture is worked up with the introduction of an inert gas stream, for example nitrogen. The product of the invention is the residue of the work-up by distillation, and is obtained as a clear low-viscosity liquid.

A particular advantage of the mixtures of oligomers of the invention is that their flashpoints are above the flashpoints of the corresponding pure alkyltrialkoxysilanes or their alcoholic solutions. Thus, the flashpoints of the mixtures of oligomers of the invention are preferably above 100° C., particularly preferably above 110° C.

The present invention further relates to the use of the present mixture of oligomers to render mineral surfaces hydrophobic.

Materials having such mineral surfaces are, for example- building materials such as concrete, cement, mortar, lime sandstone, bricks, or any type of natural rocks or else inorganic powders, for example customary fillers or pigments, aluminum oxides or aluminum oxide hydrates, such as aluminum trihydrate, silicic acids, quartz, mica, titanium oxides, zirconium oxides, hafnium oxides or titanium oxide hydrates, zirconium oxide hydrates, hafnium oxide hydrates, iron oxides or iron oxide hydrates or cobalt or cobalt oxide hydrates or else lime and clay minerals as well as micaceous iron ore, talc, zinc phosphates and calcium metaphosphates.

In a suitable manner, a mixture of oligomers of the invention can be used in the preparation of mineral substances having hydrophobic properties, in particular for pulverulent substances, preferably after applying an oxide intermediate layer, in particular a silicon oxide and/or an aluminum oxide layer.

Having generally described the invention, a further understanding can be obtained by reference to certain specific examples which are provided herein for purposes of illustration only and are not intended to be limiting unless otherwise specified.

EXAMPLE

A 2208 g amount of octyltriethoxysilane is introduced into a 4 l stirred glass reactor having vacuum, metering and distillation apparatuses and a nitrogen inlet tube, and then 168 g of water, mixed in advance with 6.9 g of 32% by weight aqueous HCl and 400 g of ethanol, are added under atmospheric pressure at 30–70° C. The clear mixture is held for approximately 2 h at approximately 77° C. under gentle reflux. A clear reaction mixture results. Ethanol is then removed by distillation, applying reduced pressure decreasing from 400 mbar to approximately 5 mbar and at a bottom temperature below 95° C. with simultaneous introduction of a nitrogen stream (approximately 7 h). 1550 g of product having the following properties are isolated:

Free ethanol (by gas chromatography):
  1.3% by weight 0.8 mol of ethoxy groups per mol of Si ($^1$H-NMR)
Viscosity: 38.8 mPa·s (DIN 53 015)
Boiling point: 280° C.
Flash point: 125° C.
Density: 0.95 g/ml
Cl content: 66 ppm by weight
Degree of oligomerization: 3–20, mean molar mass 1160 g/mol (GPC (gel permeation chromatography), SFC (supercritical fluid chromatography)).

Having now fully described the invention, it will be apparent to one of ordinary skill in the art that many changes and modifications can be made thereto without departing from the spirit or scope of the invention as set forth herein.

The subject matter of German priority application serial number 196 24 032.8 filed Jun. 17, 1996 is hereby incorporated by reference into this application.

What is claimed as new and desired to be secured by Letters Patent of the United States is:

1. A mixture of oligomers of alkylalkoxysilanes condensed in the chain and/or cyclic form having a viscosity of less than 100 mPa·s, said mixture of oligomers containing less than 2% by weight of free alcohols and the condensed alkoxysilanes satisfying formula I:

$$R'O \!-\!\!\left[\!Si(R)(OR')\!-\!O\!\right]_{\!x}\!\!-\!R', \quad (I)$$

wherein R is an alkyl group having 3 to 18 carbon atoms, and each R' is (i) methyl, ethyl or hydrogen, or is (ii) methyl or hydrogen, or is (iii) ethyl or hydrogen, the degree of oligomerization residing in the range $2 \leq x \leq 20$ and the quotient of the molar ratio [Si/alkoxy group]$\geq$1; and/or satisfying formula II:

$$\left[Si(R)(OR')\!-\!O\right]_{\!x}, \quad (II)$$

in which R is an alkyl group having 3 to 18 carbon atoms, and R' is (i) methyl, ethyl or hydrogen, or is (ii) methyl or hydrogen or is (iii) ethyl or hydrogen, the degree of oligomerization being $x \geq 3$ and the quotient of the molar ratio [Si/alkoxy group]$\geq$1, which is obtained by hydrolyzing and condensing alkyltrialkoxysilanes, wherein the silanes bear alkyl groups with 3 to 18 carbon atoms and methoxy and/or ethoxy groups as alkoxy groups, employing more than 1 mole of water per 1 mole of Si, and employing HCl as the catalyst, and distilling the reaction mixture obtained under reduced pressure at a bottom temperature <95° C.

2. The mixture of oligomers as claimed in claim 1, which has a content of alkoxy groups of greater than 0.01% by weight and less than 20% by weight, based on the weight of the mixture of oligomers present.

3. The mixture of oligomers as claimed in claim 1, wherein R is an alkyl group having in each case the same number of carbon atoms.

4. The mixture of oligomers as claimed in claim 3, wherein R is an octyl group.

5. The mixture of oligomers as claimed in claim 1, which has a flashpoint above 100° C.

6. The mixture of oligomers as claimed in claim 1, wherein alkyl group R contains 4 to 16 carbon atoms.

7. The mixture of oligomers as claimed in claim 6, wherein the alkyl group R contains 6 to 10 carbon atoms.

8. A process for preparing a mixture of oligomers as claimed in claim 1 comprising:

hydrolyzing and condensing alkyltrialkoxysilanes, wherein the silanes bear alkyl groups, having 3 to 18 carbon atoms and methoxy and/or ethoxy groups as alkoxy groups, in the presence of more than 1 mol of water per 1 mol of Si and HCl as catalyst; and working-up, by distillation, the resulting reaction mixture under reduced pressure at a bottom temperature of below 95° C.

9. The process as claimed in claim 8, wherein the hydrolysis and condensation of the alkyltrialkoxysilanes is carried out in methanol and/or ethanol as a diluent or solvent.

10. The process as claimed in claim 8, wherein the hydrolysis and condensation of the alkyltrialkoxysilanes is carried out at atmospheric pressure at a temperature between 10 and 80° C.

11. The process as claimed in claim 8, wherein an inert gas stream is passed into the reaction mixture during work-up.

12. A method of rendering mineral surfaces hydrophobic, comprising:

coating said surfaces with the mixture of oligomers of claim 1.

13. The method of claim 12, wherein the mineral is pulverulent.

* * * * *

UNITED STATES PATENT AND TRADEMARK OFFICE
CERTIFICATE OF CORRECTION

PATENT NO. : 5,932,757

DATED : August 3, 1999

INVENTOR(S): Burkhard STANDKE, et al.

It is certified that an error appears in the above-identified patent and that said Letters Patent is hereby corrected as shown below:

On the title page, item [73], the assignee's information should be:

--[73] Assignee:   Hüls Aktiengesellschaft, Marl Germany--

Signed and Sealed this

Twenty-eighth Day of November, 2000

Attest:

Q. TODD DICKINSON

*Attesting Officer*                   *Director of Patents and Trademarks*